United States Patent [19]

Shipov et al.

[11] Patent Number: 5,021,568

[45] Date of Patent: Jun. 4, 1991

[54] LACTAM-1-ACETIC ACID CARBALKOXYMETHYL ESTERS AND METHOD FOR PREPARING SAME

[76] Inventors: Alexandr G. Shipov, ulitsa Molodogvardeiskaya, 4, kv. 86, Moscow; Evgenia P. Kramarova, ulitsa Z. Kosmodemyanskoi, 17, korpus 2, kv. 19, Moskovskaya oblast, Schelkovo; Natalia A. Orlova, prospekt Vernadskogo, 99, korpus 1, kv. 57, Moscow; Jury I. Baukov, ulitsa Akademika Anokhina, 34, korpus 2, kv. 253, Moscow; Kristap M. Ziemelis, ulitsa Muryanu, 48, kv. 40, Riga, all of U.S.S.R.

[21] Appl. No.: 457,827

[22] PCT Filed: Apr. 22, 1988

[86] PCT No.: PCT/SU88/00093

§ 371 Date: Jan. 12, 1990

§ 102(e) Date: Jan. 12, 1990

[87] PCT Pub. No.: WO89/10359

PCT Pub. Date: Nov. 2, 1989

[51] Int. Cl.$^5$ ............... C07D 223/10; C07D 207/27
[52] U.S. Cl. ..................... 540/531; 548/551
[58] Field of Search ............... 548/551; 540/531

[56] References Cited

U.S. PATENT DOCUMENTS

| | | | |
|---|---|---|---|
| 4,341,290 | 7/1982 | Betzing et al. | 548/546 |
| 4,416,818 | 11/1983 | Poindexter | 548/547 |
| 4,650,878 | 3/1987 | Aschwanden et al. | 548/544 |

FOREIGN PATENT DOCUMENTS

| | | | |
|---|---|---|---|
| 215539 | 1/1984 | German Democratic Rep. | 548/546 |
| 77162 | 6/1981 | Romania | 548/543 |
| 77180 | 6/1981 | Romania | 548/547 |
| 1583163 | 1/1981 | United Kingdom | 548/547 |

OTHER PUBLICATIONS

WO/89/10359, published Nov. 2, 1989, 10 pages.

*Primary Examiner*—Robert T. Bond
*Attorney, Agent, or Firm*—Burgess, Ryan & Wayne

[57] ABSTRACT

The present invention relates to organic chemistry. Lactam-1-acetic acid carbalkoxymethyl esters have the following general formula:

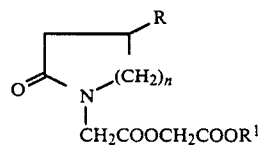

$$CH_2COOCH_2COOR^1$$

wherein with R=H, n=1 or 3; with R=phenyl, n=1; $R^1$ is an alkyl.

A method for preparing said compounds comprises reacting lactams of the general formula:

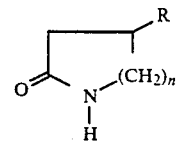

wherein with R=H, n=1 or 3, with R=phenyl n=1, with an alkali in a medium of aprotic solvents at a temperature of from 70° to 130° C., followed by the addition of an alkyl ester of a monohalcacetic acid to the resulting mixture and isolation of the desired product.

The compounds according to the present invention are intermediate products in the synthesis of known biologically active substances.

5 Claims, No Drawings

LACTAM-1-ACETIC ACID CARBALKOXYMETHYL ESTERS AND METHOD FOR PREPARING SAME

FIELD OF THE INVENTION

The present invention relates to the art of organic chemistry and, more specifically, to novel compounds, viz. lactam-1-acetic acid carbalkoxymethyl esters and to a method for preparing same. The compounds according to the present invention are intermediate compounds in the synthesis of known biologically active compounds with a peptide bond, for example 2-(2-oxo-1-pyrrolidinylacetamido)acetamide, 2-(2-oxo-4-phenyl-1-pyrrolidinylacetamido)acetamide, 2-(2-oxo-hexahydro-1-azepinylacetamido)acetamide and other compounds.

PRIOR ART

Known in the art are lactam-1-acetic acid esters and various methods for preparing same. For example, known is a method for preparing lactam-1-acetic acid esters from lactams and esters of a monohaloacetic acid using, as metallation agents, dispersed sodium hydroxide in toluene with azeotropically distilling-off water (RO, A, 77162, 77180). The resulting alkyl esters are not employed for the formation of a peptide bond with derivatives of aminoacids. The activated esters of lactam-1-acetic acid employed in the reaction of the formation of a peptide bond with aminoacid derivatives are prepared from lactams in several stages.

Thus, known in the art is a method for preparing lactam-1-acetic acid trichlorophenyl ester by reacting 1-trimethylsilyllactam with bromoacetic acid trichlorophenyl ester in the presence of propyelen oxide (SU, A, 984407); or, also known is a method of condensation of N-hydroxysuccinimide with lactam-1-acetic acid in the presence of dicyclohexylcarbodiimide resulting in the formation of corresponding esters (DD, A, 215539).

DISCLOSURE OF THE INVENTION

The compounds according to the present invention and the method for preparing same are novel and hitherto unknown from the literature.

The present invention is directed to the provision of novel compounds for the peptide synthesis of biologically active compounds by a simplified process with a high yield.

This object is accomplished by that, according to the present invention, novel compounds are claimed, viz. lactam-1-acetic acid carbalkoxymethyl esters of the general formula:

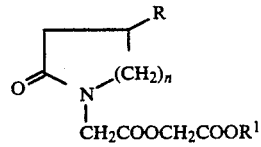

wherein with $R=H$, $n=1$ or 3, and with $B=$phenyl, $n-1$; $B^1$ is an alkyl.

The lactam-1-acetic acid carbalkoxymethyl esters are stable, viscous, colourles or slightly yellowish liquids, or low-melting white crystalline substances distillable in vacuum. Their structure is verified by methods of IR- and NMR-spectroscopy, elemental analysis or chemical transformations.

The claimed lactam-1-acetic acid carbalkoxymethyl esters are activated esters and, in contrast to known lactam-1-acetic acid alkyl esters, can be used for the formation of a peptide bond under mild conditions with derivatives of aminoacids in the synthesis of known biologically active compounds such as 2(-oxo-1-pyrrolidinylacetamido)acetamide, 2-(2-oxo-4phenyl-1-pyrrolidinylacetamido)acetamide, 2-(2-oxohexahydro-1-azepinylacetamido)acetamide and other compounds. The use of the compounds according to the present invention makes it possible to carry out the formation of a peptide bond without using conventional condensation agents usually employed in such cases, e.g. dicyclohexylcarbodiimide, as well as to elevate the yield of products of the peptide synthesis.

The method for preparing the compounds according to the present invention resides in that lactams of the general formula:

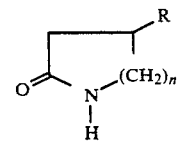

wherein with $R=H$, $n=1$ or 3, where $R=$phenyl, $n=1$ are reacted with an alkali in a medium of aprotic solvents at a temperature within the range of from 70° to 130° C., followed by the addition of an alkyl ester of a monohaloacetic acid to the resulting mixture and isolation of the desired product. In order to simplify the process, as the alkali it is advisable to use potassium hydroxide and as the aprotic solvents—dimethylsulphoxide or a mixture thereof with toluene or benzene. To increase the yield of the desired product, it is advisable that as the alkyl ester of the monohaloacetic acid use be made ethylchloroacetate or ethylbromoacetate.

The method for preparing lactam-1-acetic acid carbalkoxymethyl esters according to the present invention, as compared to the prior art method for preparing other activated esters of lactam-1-acetic acid is a single-stage one and enables high yields of the desired product.

BEST MODE FOR CARRYING OUT THE INVENTION

The method according to the present invention is performed in the following manner. A lactam is heated at a temperature within the range of from 70° to 130° C. with an alkali in an aprotic solvent till a complete dispergation of the alkali. As the alkali use can be made of potassium hydroxide or sodium hydroxide and as the aprotic solvent use can be made of, for example, dimethylsulphoxide or a mixture thereof with benzene or toluene. The reaction mixture is then added with an alkyl ester of a monohaloacetic acid such as ethylchloroacetate or ethylbromoacetate and the desired product is isolated. The isolation of the desired product is effected by way of a vacuum fractionation of the reaction mixture or by extraction of the desired product with a solvent.

The yield of the desired product is as high as 75% of the theoretical.

For a better understanding of the present invention, some specific examples illustrating the method for preparing the claimed compounds are given hereinbelow.

EXAMPLE 1

Into a three-neck flask provided with a stirrer, a dropping funnel and a reflux condenser there are charged 25.5 g (0.3 mol) of 2-pyrrolidone, 33.6 g (0.6 mol) of potassium hydroxide and 100 ml of dimethylsulphoxide. The mixture is heated on a water bath at the temperature of 70° C. under stirring till a complete dispergation of the alkali. Thereafter, dropwise added to the mixture are 73.5 g (0.6 mol) of ethylchlorcacetate and it is allowed to stand at room temperature for several hours. Then the mixture is filtered, the filtrate is fractionated to give 38 g (55.3%) of (2-oxo-1-pyrrolidinyl)acetic acid carboethoxyemthyl ester, b.p. 197°-200° C. (11 mm Hg), $n_D^{20} = 1.4700$.

IR spectrum ($\nu$, cm$^{-1}$ solution of ClCH$_2$HC$_2$Cl): 1,730 (C=O, ester), 1,675 (O=O, lactam). NMB spectrum ($\delta$, ppm, CDCl$_3$): 1.26 t (CH$_3$, J 7 Hz), 2.09 m and 2.36 m (CH$_2$CH$_2$CO cycle, J 7 Hz), 3.50 m (NCH$_2$ cycle, J 6.6 Hz), 4.16 s (CH$_2$N), 4.20 g (OCH$_2$CH$_3$ J 7 Hz), 4.36 s (OCH$_2$CO).

Found, %: C 52.25 H 6.66 N 6.19 C$_{10}$H$_{15}$NO$_5$. Calculated, %: C 52.39 H 6.59 N 6.11.

EXAMPLE 2

In a manner similar to that described in the foregoing Example 1, from 25.5 g (0.3 mol) of 2-pyrrolidone, 16.8 g (0.3 mol) of potassium hydroxide, 100 ml of dimethylsulphoxide and 36.8 g (0.3 mol) of ethylchloroacetate there are obtained 17.6 g (25.6%) of carboethoxymethyl ester of (2-oxo-1-pyrrolidinyl)acetic acid, b.p. 197°-200° C. (10 mm Hg), $n_D^{20} = 1.4705$.

EXAMPLE 3

The process is carried out in a manner similar to that described in Example 1 hereinbefore.

Use is made of 25.5 g (0.3 mol) of 2-pyrrolidone, 50.4 g (0.9 mol) of potassium hydroxide in 200 ml of dimethylsulphoxide and 115 g (0.94 mol) of ethylchloroacetate. After keeping the reaction mass of room temperature, it is added with 600 ml of water and extracted 3 times with portions of 100 ml of dichoroethane. The combined extracts are evaporated, the residue is subjected to fractionation to give 46.9 g (68%) of 2-oxo-1-pyrrolidinyl)acetic acid carboethoxymethyl ester, b.p. 197°-200° C. (10 mm Hg), $n_D^{20} = 1.4703$.

EXAMPLE 4

A mixture of 25.5 g (0.3 mol) of 2-pyrrolidone, 33.6 g (0.6 mol) of potassium hydroxide, 150 ml of dimethylsulphoxide and 100 ml of benzene are refluxed under stirring till a complete dispergation of the alkali. Dropwise added to the mixture are 73.5 g (0.6 mol) of ethylchloroacetate and heating at reflux is continued for additional 2 hours, whereafter the temperature of the mixture is brought to room temperature. The salt residue is filtered-off, the mixture is subjected to fractionation to give 35.7 g (52%) of (2-oxo-1-pyrrolidinyl)-acetic acid carboethoxymethyl ester, b.p. 195°-198° C. (9 mm Hg), $n_D^{20} = 1.4706$.

EXAMPLE 5

A mixture of 25.5 g (0.3 mol) of 2-pyrrolidone, 40 g (1 mol) of sodium hydroxide in 200 ml of dimethylsulphoxide is intermixed at the temperature of 90° C. till a complete dispergation of the alkali, whereafter the mixture is dropwise added with 122.5 g (1 mol) of ethylchloroacetate and allowed to stand at room temperature for several hours. Then added to the mixture are 600 ml of water and the mixture is subjected to extraction for 3 times by portions of 100 ml of chloroform, the combined extracts are evaporated, the residue is subjected to fractionation to give 39 g (56.8%) of (2-oxo-1-pyrrolidinyl)acetic carboethoxymethyl ester, b.p. 195°-199° C. (10 mm Hg), $n_D^{20} = 1.4705$.

EXAMPLE 6

A mixture of 25.5 g (0.3 mol) of 2-pyrrolidone, 33.6 g (0.6 mol) of potassium hydroxide and 200 ml of dimethylsulphoxide is intermixed at the temperature of 70° C. till a complete dispergation of the alkali; then the mixture is dropwise added with 100.2 g (0.6 mol) of ethylbromoacetate and allowed to stand for several hours at room temperature. The mixture is diluted with 600 ml of water and extracted 3 times with portions of 100 ml of chloroform. The combined extracts are evaporated, the residue is subjected to fractionation to give 42.6 g (62%) of (2-oxo-1-pyrrolidinyl)acetic acid carboethoxymethyl ester, b.p. 196°-198° C. (9 mm Hg), $n_D^{20} = 1.4701$.

EXAMPLE 7

70 g (1.25 mol) of potassium hydroxide are fully dispersed in 500 ml of dimethylsulphoxide and 80.5 g (0.5 mol) of 4-phenyl-2-pyrrolidone at a temperature of 110°-115° C. Dropwise added to the mixture are 153 g (1.25 mol) of ethylchloroacetate and allowed to stand a room temperature for one day. The mixture is diluted with 1.5 l of water and extracted for 2 times with portions of 200 ml of benzene. The combined extracts are evaporated, the residue is fractionated to give 79 g (52%) of (2-oxo-4-phenyl-1-pyrrolidinyl)acetic acid carboethoxymethyl ester, b.p. 220°-223° C. (1.5 mm Hg), $n_D^{20} = 1.5215$. IR spectrum ($\nu$,cm$^{-1}$,CCl$_4$): 1.745 (C=O, ester), 1,700 (C=O, lactam). PMR spectrum ($\delta$, ppm, CDCl$_3$): 1.27 t (CH$_3$, J 6 Hz), 2.75 m (CH$_2$CO cycle), 3.70 m (CHCH$_2$N cycle), 4.20 q (OCH$_2$CH$_3$J 6 Hz), 4.25 s (NCH$_2$SO), 4.66 s (OCH$_2$CO), 7.29 s (C$_6$H$_5$).

NMR $^{13}$C ($\delta$, ppm, CDCl$_3$): 14.05, 37.20, 38.30, 43.70, 54.50, 61.13, 61.45, 126.81, 127.01, 128.76, 142.29, 167.13, 168.11, 174.35.

Found, %: C 62.86; H 6.22; N 4.62. C$_{16}$H$_{19}$NO$_5$. Calculated, %: C 62.94; H 6.27; N 4.59.

EXAMPLE 8

45 g (0.8 mol) of potassium hydroxide are dispersed in a mixture of 300 ml of dimethylsulphoxide and 40 g (0.248 mol) of 4-phenyl-2-pyrrolidone at the temperature of 100° C.; thereafter, 120 g (0.98 mol) of ethylchloroacetate are added dropwise and the mixture is allowed to stand at room temperature for several hours. The mixture is diluted with 800 ml of water and extracted for 3 times with 100 ml portions of benzene. The combined extracts are evaporated, the residue is subjected to fractionation to give 55.7 g (75.6%) of (2-oxo-4-phenyl-1-pyrrolidinyl)acetic acid carboethoxymethyl ester, b.p. 210°-214° C. (1 mm Hg), $n_D^{20} = 1.5210$.

EXAMPLE 9

A mixture of 80.5 g (0.5 mol) of 4-phenyl-2-pyrrolidone, 70 g (1.25 mol) of potassium hydroxide, 500 ml of dimethylsulphoxide and 150 ml of toluene are heated at reflux under stirring at the reaction mixture temperature of 130° C. till a complete dispergation of the alkali, whereafter the mixture is dropwise added with 153 g (1.25 mol) of ethylchloroacetate and allowed to stand at room temperature for one day. The mixture is diuted with 1.2 l of water and extracted twice with 100 ml portions of toluene; the extracts are subjected to fractionation to give 73.2 g (47%) of (2-oxo-4-phenyl-1-pyrrolidinyl)acetic acid carboethoxymethyl ester, b.p. 210°–214° C. (1 mm Hg), $n_D^{20} = 1.5212$.

EXAMPLE 10

To a dispersion of 30 g(0.75 mol) of sodium hydroxide in 250 ml of dimethylsulphoxide and 40.3 g (0.25 mol) of 4-phenyl-2-pyrrolidone prepared at a temperature of 110°–115° C. 92 g (0.75 mol) of ethylchloroacetate are added, the mixture is heated at 90° C. for two hours and brought to room temperature afterwards. The mixture diluted with 750 ml of water is extracted 3 times with 70 ml portions of benzene. The extracts are subjected to fractionation to isolate 42 g (55%) of (2-oxo-4-phenyl-1-pyrrolidinyl) acetic acid carboethoxymethyl ester, b.p. 211°–214° C. (1 mm Hg), $n_D^{20} = 1.5210$.

EXAMPLE 11

To a dispersion of 28 g (0.5 mol) of potassium hydroxide in 200 ml of dimethylsulphoxide and 40.3 g (0.25 mol) of 4-phenyl-2-pyrrolidone obtained at the temperature of 100° C. 83.5 g (0.5 mol) of ethylbromoacetate are added. One day after, the reaction mixture is added with 600 ml of water and extracted 2 times with 100 ml portions of benzene. The benzene extracts are fractionated to isolate 46 g (60%) of (2-oxo-4-phenyl-1-pyrrolidinyl-)acetic acid carboethoxymethyl ester, b.p. 210°–213° C. (1 mm Hg), $n_D^{20} = 1.5212$.

EXAMPLE 12

A mixture of 33.9 g (0.3 mol) of ε-caprolactam, 33.6 g (0.6 mol) of potassium hydroxide in 100 ml of dimethylsulphoxide is intermixed upon heating to the temperature of 100° C. till a complete dispergation of the alkali, whereafter 73.5 g (0.76 mol) of ethylchloroacetate are dropwise added to the mixture which is allowed to stand at room temperature for several hours. The mixture is diluted with 40 ml of water and extracted for 3 times with 100 ml portions of chloroform. The extracts are subjected to fractionation to isolate 38.9 g (50.5%) of (2-oxohexahydro-1-azepinyl)acetic acid carboethoxymethyl ester, b.p. 210°–213° C. (12 mm Hg), m.p. 33.5°–35° C. (diethyl ether).

IR spectrum ($\nu$, cm$^{-1}$, CHCl$_3$): 1.745 (C=O, ester) 1.635 (C=O, lactam).

PMR spectrum (δ, ppm, CCl$_4$): 1.23 t (CH$_3$, J 6 Hz), 1.69 m (3CH$_2$ cycle), 2.42 m (CH$_2$CO cycle), 3.41 m (CH$_2$N cycle), 4.12 q (CH$_2$O, J 6 Hz), 4.18 s (NCH$_2$OC), 4.58 s (OCH$_2$CO).

Found, %: C 55.90; H 7.49; N 5.41. C$_{12}$H$_{19}$NO$_5$. Calculated, %: C 56.02; H 7.44; N 5.44.

EXAMPLE 13

In a manner similar to that described in the foregoing Example 12 from 22.6 g (0.2 mol) of ε-caprolactam, 39.2 g (0.7 mol) of granulated potassium hydroxide, 200 ml of dimethylsulphoxide and 85.8 g (0.7 mol) of ethylchloroacetate there are obtained 30 g (58.4%) of (2-oxohexahydro-1-azepinyl)acetic acid carboethoxymethyl ester, b.p. 155°–157° C. (1 mm Hg), m.p. 34°–35° c. (diethyl ether).

INDUSTRIAL APPLICABILITY

Carbalkoxymethyl esters of lactam-1-acetic acid according to the present invention are useful in the synthesis of biologically active substances such as 2-(2-oxo-1-pyrrolidylacetamido)acetamide, 2-(2-oxohexahydro-1-azepinylacetamido)-acetamide, 2-(2-oxo-4-phenyl-1-pyrrolidinylacetamido)-acetamide and other compounds exhibiting activity in respect to processes associated with improvement of memory and a protective effect in the case of oxygen deficiency.

We claim:

1. Lactam-1-acetic acid carbalkoxymethyl esters of the general formula:

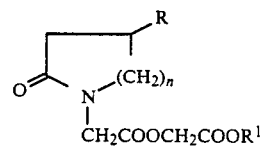

wherein with R=H, n=1 or 3; R=phenyl, n=1; R$^1$=an alkyl.

2. A method for preparing lactam-1-acetic acid carbalkoxymethyl esters according to claim 1, characterized in that lactams of the general formula;

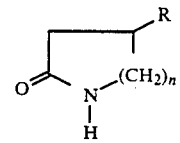

wherein with R=H, n=1 or 3; R=phenyl, n=1 are reacted with an alkali in a medium of an aprotic solvent at a temperature within the range of from 70° to 130° C., followed by the addition of an alkyl ester of a monohaloacetic acid to the resulting mixture and isolation of the desired product.

3. A method according to claim 2, characterized in that as the alkali use is made of potassium hydroxide or sodium hydroxide.

4. A method according to any one of claims 2–3, characterized in that as the aprotic solvents use is made of dimethylsulphoxide or a mixture thereof with toluene or benzene.

5. A method according to any one of claims 2 to 4, characterized in that as the alkyl ester of the monochaloacetic acid use is made of ethylchloroacetate or ethylbromoacetate.

* * * * *